United States Patent [19]

Dumoulin

[11] Patent Number: 5,285,260
[45] Date of Patent: * Feb. 8, 1994

[54] SPECTROSCOPIC IMAGING SYSTEM WITH ULTRASONIC DETECTION OF ABSORPTION OF MODULATED ELECTROMAGNETIC RADIATION

[75] Inventor: Charles L. Dumoulin, Ballston Spa, N.Y.

[73] Assignee: General Electric Company, Schenectady, N.Y.

[*] Notice: The portion of the term of this patent subsequent to Oct. 22, 2008 has been disclaimed.

[21] Appl. No.: 909,275

[22] Filed: Jul. 6, 1992

[51] Int. Cl.$^5$ .............................................. G01J 3/52
[52] U.S. Cl. ................................... 356/432; 356/345; 356/357; 356/358; 356/360
[58] Field of Search ............... 356/432, 345, 355, 357, 356/358, 360

[56] References Cited

U.S. PATENT DOCUMENTS

| | | | |
|---|---|---|---|
| 4,044,257 | 8/1977 | Kreuger | 250/344 |
| 4,581,939 | 4/1986 | Takahashi | 356/432 X |
| 4,710,030 | 12/1987 | Tauc et al. | 356/432 |
| 4,750,822 | 6/1988 | Rosencwaig et al. | 356/445 |
| 4,784,494 | 11/1988 | Pawliszyn | 356/432 |
| 4,808,828 | 2/1989 | Kitamori et al. | 250/458.1 |
| 4,874,251 | 10/1989 | Thomas et al. | 356/432 |
| 5,060,248 | 10/1991 | Dumoulin | 378/53 |
| 5,062,715 | 11/1991 | Nakata et al. | 356/432 |
| 5,136,172 | 8/1992 | Nakata et al. | 356/432 |
| 5,170,217 | 12/1992 | Nishimoto et al. | 356/345 X |

FOREIGN PATENT DOCUMENTS

352789  1/1990  European Pat. Off. .

Primary Examiner—Robert J. Warden
Assistant Examiner—Krisanne M. Thornton
Attorney, Agent, or Firm—Lawrence P. Zale; Marvin Snyder

[57] ABSTRACT

An optical interferometer and an ultrasonic distance measuring subsystem are used to obtain spectra from the surface of a sample. The interferometer uses a broadband electromagnetic radiation source and modulates the radiation at a frequency which is inversely proportional to wavelength. The modulated radiation impinges on the surface of interest where it is absorbed. The absorption of radiation causes the surface of the sample to expand. This change in dimension is then detected by the ultrasonic distance measuring subsystem which employs a single frequency acoustic radiation source to measure the instantaneous distance between the sample surface and the ultrasonic distance measurement subsystem. The detected changes in distance relate to amplitude of absorption at a given wavelength, thereby allowing absorption spectra for surface point to be generated indicating the chemical composition of each point of the surface.

10 Claims, 6 Drawing Sheets

SPECTROSCOPIC IMAGING SYSTEM WITH ULTRASONIC DETECTION OF ABSORPTION OF MODULATED ELECTROMAGNETIC RADIATION

CROSS REFERENCE TO RELATED APPLICATIONS

This application is related to applications "SPECTROSCOPIC IMAGING SYSTEM USING A PULSED ELECTROMAGNETIC RADIATION SOURCE AND AN INTERFEROMETER", Ser. No. 07/909,276 filed Jul. 6, 1992 "DUAL INTERFEROMETER SPECTROSCOPIC IMAGING SYSTEM" Ser. No. 07/909,277 filed Jul. 6, 1992 both by Charles L. Dumoulin, both filed simultaneously with this application, and both assigned to the present assignee.

BACKGROUND OF THE INVENTION

1. Field of the Invention

The present invention relates to optical spectroscopy and more particularly to the optical spectroscopy of a surface of a sample.

2. Description of Related Art

Absorption and transmission spectra of a sample can be obtained using electromagnetic radiation for the purpose of identifying chemical types. Certain spectral regions are of greater use than others. The spectral regions of greatest use are those in which chemical species contained within the sample absorb radiation at characteristic wavelengths. The absorbed radiation can be detected directly, re-emitted by the sample or cause the sample to fluoresce. Spectroscopic measurements of absorption, emission and fluorescence using infra-red, visible and ultra-violet light are widely used for sample analysis. Unfortunately, many of these techniques are not well suited to applications where the sample has rough surfaces. Radiation is scattered by rough surfaces thereby making measurement of reflection or transmission difficult. Techniques requiring transmission through a sample are difficult or impossible using opaque samples.

One technique which has proved useful for the spectroscopic analysis of rough surfaces is Photo-Acoustic Spectroscopy. With this technique, a monochromatic light source is chopped to create a pulsed light source. The pulsed light is directed to impinge on the surface of the sample. The pulsed light is at a wavelength which is absorbed by the sample, causing a periodic heating of the surface which in turn causes the surface to expand and contract. This movement generates sound waves which propagate through the gas above the surface and are detected by a sensitive microphone. Spectra of the surface are generated by varying the wavelength of the incident radiation. Unfortunately, the detection efficiency of Photo-Acoustic procedures is low with respect to other optical analysis methods, and thus the technique is not easily applied to small samples.

Presently there is a need for an analytical system capable of detecting the optical spectra of selected chemical types for samples having rough surfaces, with high sensitivity.

SUMMARY OF THE INVENTION

A spectroscopic imaging system according to the invention is comprised of an interferometer and an ultrasonic distance measuring subsystem. The interferometer employs a broadband electromagnetic radiation source. A movable mirror of the interferometer is moved linearly, causing the amplitude of each different wavelength produced by the broadband radiation source to be modulated at a frequency which is inversely proportional to its respective wavelength. The modulated light impinges on the surface of a sample of interest, where it is absorbed causing the temperature of the surface to rise and the surface to expand. Since the radiation is modulated (i.e. the amplitude of a selected wavelength varies sinusoidally with time) heating of the surface is periodic. This results in a periodic expansion and contraction of the surface at a rate which is inversely proportional to the wavelength of the absorbed radiation.

An ultrasonic distance measuring system reflects single frequency sound off of the sample surface. The wavelength of ultrasonic source is chosen to minimize absorption of the radiation by the sample surface and to minimize the size of an ultrasonic focal spot. The reflected sound is used by the ultrasonic distance measuring subsystem to measure the instantaneous distance between the sample surface and the subsystem. This distance varies with time at a frequency inversely proportional to the wavelength of radiation absorbed from the broadband radiation source. The amplitude of the distance changes is proportional to the degree of absorption of the broadband radiation source; therefore, the changes in distance measured by the ultrasonic distance measuring system are an indication of the absorption properties of the sample surface.

In a second embodiment of the invention, the interferometer is replaced with a monochromatic light source which is chopped at a selected frequency. The monochromatic light source may be comprised of a tunable laser or a broadband light source/monochromator combination. With this embodiment, optical spectra are obtained responsive to scanning the wavelength of the monochromatic radiation over a selected range of values.

OBJECTS OF THE INVENTION

It is an object of the invention to provide a system for obtaining absorption spectra from a rough surface of a sample.

It is another object of the invention to provide a system for obtaining absorption spectra from a non-transparent sample.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
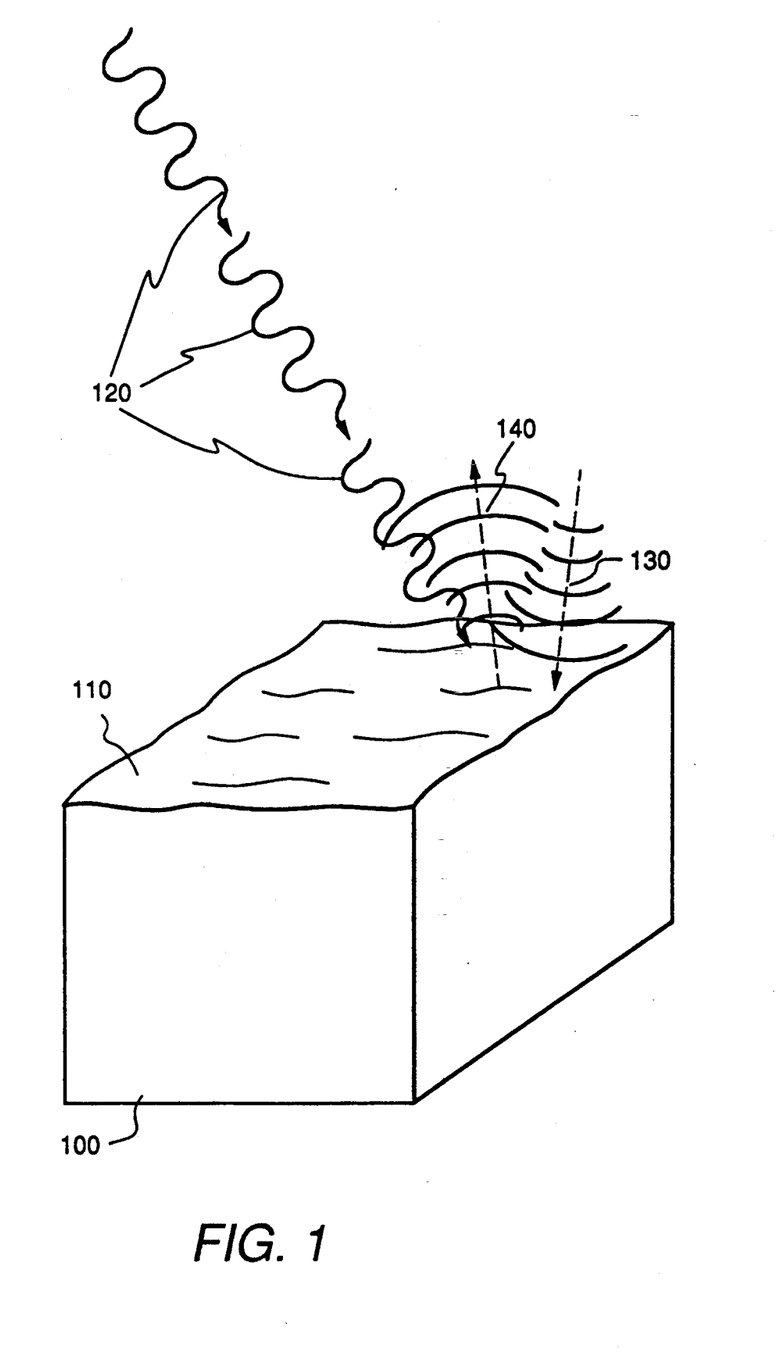
FIG. 1 is a perspective view of a sample surface absorbing radiation from one source and reflecting ultrasonic waves from an ultrasound source.

FIG. 1 shows a sample 100 having a surface 110 to be analyzed. A sample excitation beam 120 of electromagnetic radiation impinges upon surface 110, which is a rough surface. A portion of sample excitation beam 120 is absorbed by surface 110 which is characteristic of specific chemical components.

A measurement beam 130 of acoustic radiation from an ultrasonic distance measuring subsystem impinges on rough surface 110 and is reflected thereby to produce a return beam 140 of acoustic radiation. The wavelength of the ultrasonic source for measurement beam 130 is chosen to minimize absorption of this beam by sample 100. Return beam 140 is scattered by the rough surface, but a sufficient amount of radiation is reflected back to the ultrasonic distance measuring subsystem where it is used to make an accurate measurement of the displacement of surface 110 with respect to the ultrasonic distance measuring subsystem.

Figure 2:
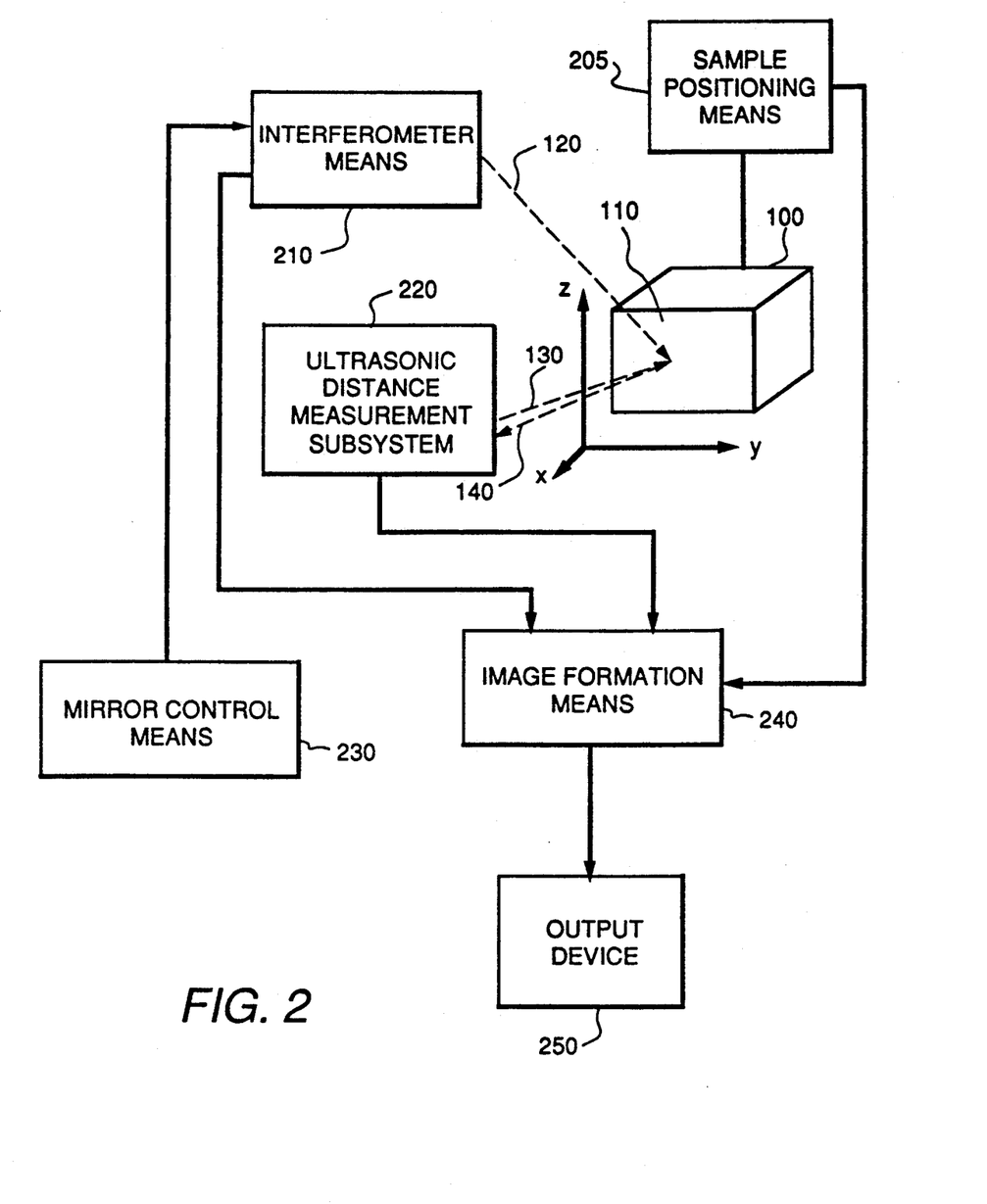
FIG. 2 is a block diagram of a first embodiment of the present invention in which interferometer means and an ultrasonic distance measurement subsystem are used to obtain absorption spectra from a selected sample surface.

FIG. 2 is a schematic diagram of one embodiment of the present invention. Here, sample 100 is shown positioned at a desired location in three dimensions (x,y,z) relative to the system by a sample positioning means 205. The surface 110 of sample 100 is then irradiated with radiation from interferometer means 210 and ultrasonic distance measuring subsystem 220. A mirror control means 230 is used to control the motion of mirrors (not shown in FIG. 2) within interferometer means 210. Signals indicating the motion of the mirrors in interferometer means 210 are sent from interferometer means 210 to an image formation means 240. Signals from ultrasonic distance measuring subsystem means 220 are supplied to image formation means 240 substantially simultaneously with the mirror motion information. Signals indicating the position of sample 100 are sent from sample positioning means 205 to image formation means 240. The image formation means 240 employs the signals provided by the interferometer means 210, ultrasonic distance measurement means 220, and sample position means 205 to generate absorption spectra for a plurality of irradiated points on sample surface 110. An output device 250 manipulates selected portions of the spectra to create maps of chemical types on surface 110. Output device 250 may also execute a number of analytical tests based upon the spatial and spectral information.

Figure 3:
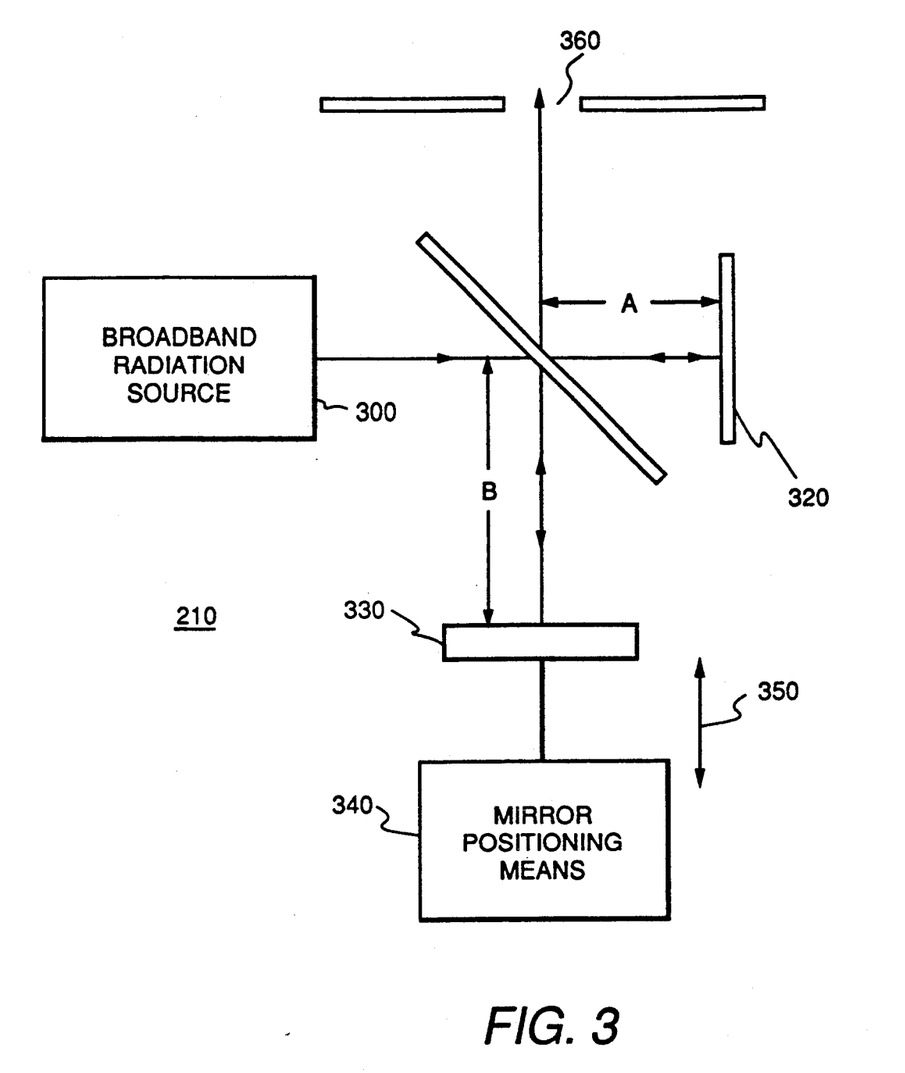
FIG. 3 is a block diagram of one embodiment of the interferometer means of FIG. 2 used to generate radiation directed at the surface of the sample.

FIG. 3 is a detailed schematic illustration of interferometer 210 having a broadband radiation source 300 which transmits radiation to a beam splitter means 310, such as a half-silvered mirror. The beam splitter means 310 splits the radiation from source 300 into a first transmitted beam and a first reflected beam. The first transmitted beam reflects off of a fixed mirror 320 situated at a distance A from beam splitter 310 back to the beam splitter which thereupon creates a second transmitted beam and a second reflected beam from the reflected first transmitted beam. The first reflected beam is reflected at a distance B from the beam splitter by a movable mirror 330 that is in motion, and impinges upon beam splitter 310 to form a third reflected beam and a third transmitted beam. A mirror positioning means 340, controlled by mirror control means 230 of FIG. 2, causes a constant motion of movable mirror 330. When path lengths A and B of the radiation reflected from the fixed and moveable mirrors are equal, the second reflected and third transmitted beams are in phase as they pass through an exit port 360 of the interferometer. As the mirror position is varied along its movement axis 350, path lengths A and B are no longer equal and the two beams have a phase relationship determined by the difference in path lengths and the wavelength of the radiation; that is, they constructively and destructively interfere with each other causing modulation of amplitude for each wavelength. For example, if movable mirror 330 is positioned such that the difference in path lengths is an integral number of wavelengths, the two beams, for a given wavelength, will be in phase as they exit the interferometer, and will combine constructively. If, on the other hand, the path lengths differ by ½ the wavelength of the radiation, the two beams will be 180° out of phase, for a given wavelength, as they exit the interferometer, and will combine destructively so that no net radiation at that frequency will exit the interferometer.

Broadband radiation source 300 in the interferometer generates radiation having a distribution of wavelengths. If path lengths A and B are equal, all wavelengths of the radiation from the broadband source will be propagated through the interferometer. As the movable mirror changes position, radiation at each wavelength will go in and out of phase. If the mirror movement is constant with time, the radiation exiting the interferometer will be modulated at a frequency which is inversely proportional to the wavelength of the radiation.

The broadband radiation from interferometer means 210 impinges upon the surface 110 of sample 100 of FIG. 1 where some fraction of it is absorbed. The absorption of radiation causes the temperature of the immediate area of the surface to rise. This rise in temperature in turn causes the material in the surface to expand. Since the radiation is modulated (i.e. the amplitude of a selected wavelength varies sinusoidally with time), heating of the surface is periodic. This results in a periodic expansion and contraction of the surface at a rate which is inversely proportional to the wavelength of the absorbed radiation. This expansion and contraction is accurately measured with the ultrasonic distance measuring subsystem.

Figure 4:
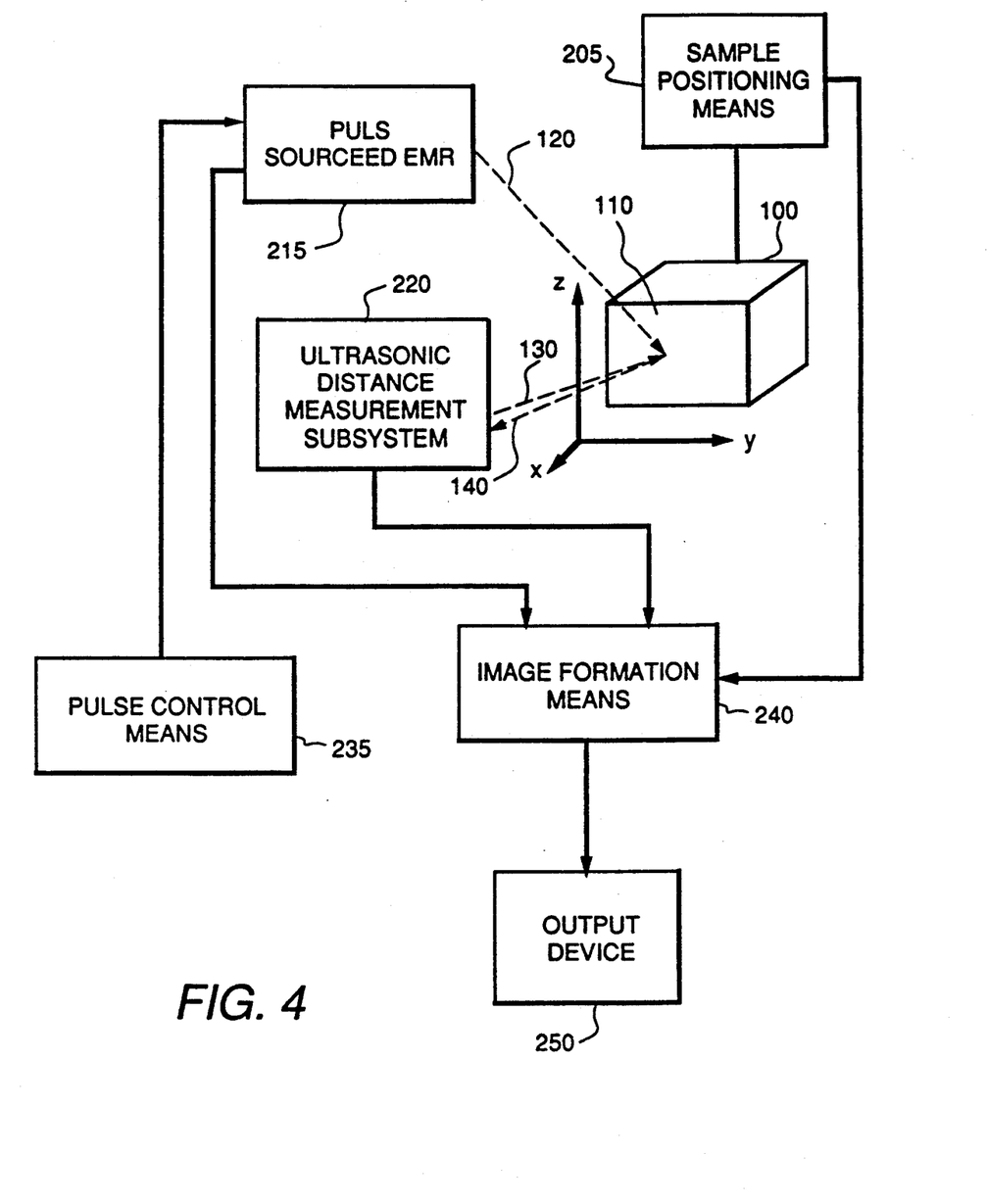
FIG. 4 is a block diagram of second embodiment of the present invention in which modulated electromagnetic radiation is generated by a pulsed electromagnetic radiation (EMR) source.

FIG. 4 is a schematic diagram of a second embodiment of the present invention. In this embodiment sample 100 is positioned at a desired location in three dimensions (x,y,z) relative to the system by a sample positioning means 205. Surface 110 of sample 100 of FIG. 1 is then irradiated with radiation from a pulsed electromagnetic radiation (EMR) source 215 and an ultrasonic distance measurement subsystem 220. A pulse control means 235 is used to control the wavelength and modulation of pulsed EMR source 215. A signal representing the wavelength and pulsing frequency from pulsed EMR source 215 is sent to an image formation means 240. Electronic signals from ultrasonic distance measurement subsystem 220 are applied to image formation means 240 substantially simultaneously with the singal from pulsed EMR source 215. The image formation means 240 employs the signals provided by the pulsed EMR source 215 and the ultrasonic distance measurement subsystem 220 to generate absorption spectra for a plurality of points on sample surface 110. An output device 250 manipulates selected portions of the spectra to create maps of chemical types on surface 110. Output device 250 may also execute a number of analytical tests based upon the spatial and spectral information.

Figure 5:
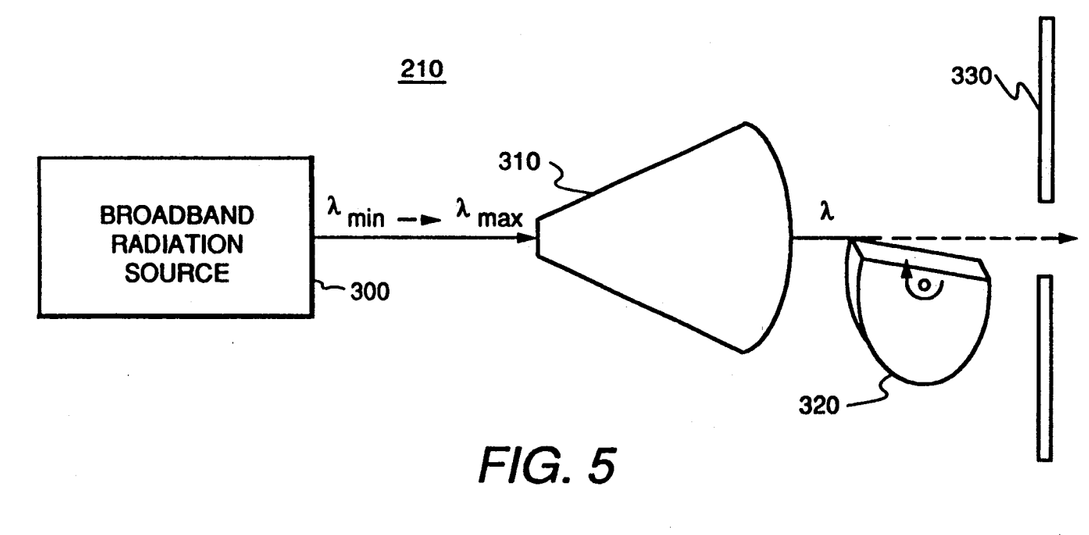
FIG. 5 is a block diagram of one embodiment of the pulsed EMR source of FIG. 4 used to generate electromagnetic radiation directed at the surface of said sample.

FIG. 5 is a schematic diagram of pulsed EMR source 215 which includes a broadband radiation source 500 that sends a beam having an array of wavelengths $\lambda_{min} \rightarrow \lambda_{max}$ to a monochromator means 510. Monochromator means 510 propagates a narrow selected band of wavelengths $\lambda$. (In alternative embodiment of the invention, a tunable laser, capable of radiating a selected wavelength may be used. The monochromator radiation, such as light enters a chopping means 520 where the light beam is interrupted at a selected frequency. The result is pulsed radiation having a wavelength $\lambda$ which exits pulsed EMR source 215 through an exit port 530. In an alternative embodiment, the chopping means 520 may be situated between broadband radiation source 500 and monochromator means 510).

As shown in FIG. 4, the pulsed radiation from pulsed EMR source 215 impinges at a spot on surface 110 of sample 100, where some fraction of the radiation is absorbed, causing the temperature of the surface in the immediate area of the spot to rise. This rise in temperature in turn causes the material of the surface to expand. Since the radiation is pulsed, heating of surface 110 is periodic, resulting in a periodic expansion and contraction of surface 110 at the pulsing frequency. This expansion and contraction is accurately measured with ultrasonic distance measurement subsystem 220.

In both embodiments of the present intervention, a Fourier transform may be performed on the measured changes in distance acquired over time d(t) to arrive at D(f) a spectrum of absorption amplitude vs. frequency of absorption for each irradiated spot on the sample surface.

Figure 6:
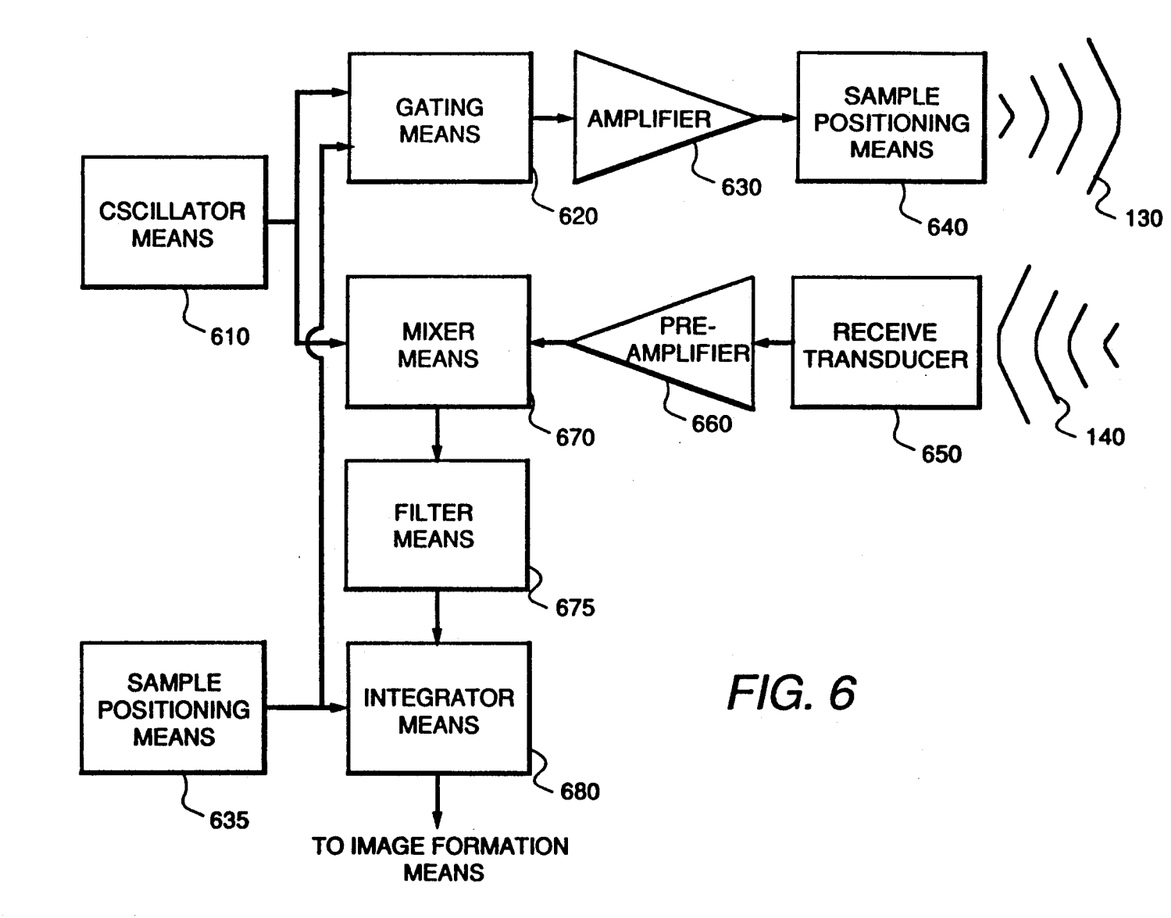
FIG. 6 is a block diagram of an embodiment of the ultrasonic distance measurement subsystem of FIG. 2 and FIG. 4.

FIG. 6 illustrates one embodiment of ultrasonic distance measurement subsystem 220 employed in the present invention. The ultrasonic distance measurement subsystem is comprised of an oscillator means 610 which generates a signal which is a substantially continuous sine wave at a selected frequency. This signal is supplied by a gating means 620 to an amplifier 630 through whenever the gating means is rendered conductive in response to a controller means 635. The amplified signal is supplied to a transmit transducer 640 which converts the signal into ultrasonic energy so as to form an acoustic measurement beam 130. The transducer may be comprised of a piezoelectric material. A return beam 140 is generated by reflection of acoustic measurement beam 130. Return beam 140 impinges on a receive transducer 650 which converts the acoustic energy into an electrical signal that supplied to a preamplifier 660. The signal from preamplifier 660 is supplied to a mixer means 670 where it is mixed with the original transmitted signal to create a signal having Doppler shift information. The mixed signal is passed to an integrator means 680 where the Doppler shift information is decoded to arrive at distance changes between ultrasonic distance measurement subsystem 220 and sample surface 110 of FIG. 1.

In an alternative embodiment, controller means 635 of ultrasonic distance measurement subsystem 220, causes gating means 620 to pass a pulsed signal. The time delay between creation of the pulse by gating means 620 and detection of signal at integrator means 680 is then used to determine the distance between surface 110 (FIG. 1) and the transducers.

While several presently preferred embodiments of the novel spectroscopic imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A system for creating images of chemical composition of a sample surface based upon the electromagnetic absorption spectra comprising:
    a) interferometer means for irradiating a portion of a sample surface with a time modulated sample excitation beam having a plurality of frequencies, each frequency having an amplitude varying with time inversely according to its frequency;
    b) ultrasonic distance measurement means for detecting changes in distance over time between the irradiated portion of said sample surface and the ultrasonic distance measurement means responsive to absorption by the sample of the broadband sample excitation radiation beam generated by the interferometer means; and
    c) image formation means for calculation of absorption spectra of the portion of said sample surface from the detected changes in distance versus time between said sample surface and the ultrasonic distance measurement subsystem for creating absorption spectra for portions of said sample surface from the detected changes in distance indicating chemical composition of said sample surface, and creating an image indicating chemical composition over the portions of said sample surface.

2. The system of claim 1 further comprising positioning means for moving said sample relative to the interferometer means and ultrasonic distance measurement subsystem.

3. The system of claim 1, wherein the interformeter means is comprised of:
    a1) a beam splitter for creating a partially transmitted and reflected beam from an incident beam;
    a2) a broadband radiation source for creating a broadband radiation beam incident upon the beam splitter so as to cause the beam splitter to create a first transmitted beam and a first reflected beam;
    a3) a fixed mirror for reflecting the first transmitted beam back toward the beam splitter, which is split by the beam splitter into a second transmitted and a second reflected beam; and
    a4) a movable mirror being movable in a substantially uniform manner for reflecting the first reflected beam back to the beam splitter so as to be split into a third transmitted beam and a third reflected beam such that the third transmitted beam constructively and destructively interferes with the second reflected beam to create a time modulated sample excitation beam having a plurality of frequencies, each frequency having an amplitude, varying with time inversely according to its frequency.

4. The system of claim 1, wherein the said ultrasonic distance measurement subsystem comprises means for simultaneously determining changes in distance between the ultrasonic distance measurement subsystem and at least one point on said sample surface versus time, thereby obtaining spatially resolved information from the irradiated portion of said sample surface.

5. The system of claim 1, wherein said image formation means comprises means responsive to the detected changes in distances therefrom, versus time obtained by said ultrasonic distance measurement subsystem and responsive to broadband radiation generated by the interferometer means in order to generate images of said sample surface.

6. The system of claim 3, wherein the broadband radiation source comprises means for generating radiation at a wavelength in one of the group of wavelengths consisting of: infra-red wavelengths, visible light wavelengths and ultraviolet wavelengths.

7. The system of claim 1, wherein the image formation means includes Fourier transformation means for calculating Fourier transform values of the detected changes in distance versus time for at least one point of the irradiated portion of said sample surface to generate an absorption spectrum for the at least one point.

8. The system of claim 1 further including an output device for creating from the absorption spectrum of the portion of said sample surface, an image showing distribution of a desired chemical type.

9. A method of creating images representing chemical composition of a sample surface based upon the electromagnetic absorption spectra thereof, comprising the steps of:
   a) irradiating a portion of said sample surface with a time modulated sample excitation beam having a plurality of frequencies, each frequency having an amplitude which varies with time inversely according to its frequency causing said sample surface to absorb a portion of the excitation beam and expand periodically changing distance between the sample surface and a measurement point;
   b) measuring the distance between the sample surface and the measurement point over time using an ultrasonic distance measurement means; and
   c) creating absorption spectra for portions of said sample surface from the detected changes in distance indicating chemical composition of said sample surface.

10. The method of claim 9, wherein the step of measuring the distance comprises the steps of:
   b1) transmitting an ultrasonic measurement beam to said sample surface;
   b2) creating an electronic signal from a detected return beam reflected from said sample;
   b3) creating an electronic signal from the transmitted ultrasonic measurement beam;
   b4) mixing the electronic signals from the return beam with the electronic signal from the transmitted ultrasonic measurement beam to create a mixed electronic signal;
   b5) sampling the mixed electronic signal over time to obtain Doppler data; and
   b6) calculating changes in distance between said sample surface and the measurement point by calculating Doppler shifts from the Doppler data.

* * * * *